(12) United States Patent
Kinkade et al.

(10) Patent No.: US 8,604,254 B2
(45) Date of Patent: Dec. 10, 2013

(54) REDUCTIVE HYDROFORMYLATION OF AN ALKYLENE TO AN ALKANOL

(75) Inventors: Nancy Kinkade, Kingsport, TN (US); Richard M. Wehmeyer, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 98 days.

(21) Appl. No.: 13/395,692

(22) PCT Filed: Nov. 2, 2010

(86) PCT No.: PCT/US2010/055111
§ 371 (c)(1),
(2), (4) Date: Mar. 13, 2012

(87) PCT Pub. No.: WO2011/059855
PCT Pub. Date: May 19, 2011

(65) Prior Publication Data
US 2012/0226079 A1    Sep. 6, 2012

Related U.S. Application Data

(60) Provisional application No. 61/260,119, filed on Nov. 11, 2009.

(51) Int. Cl.
*C07C 29/141* (2006.01)
*C07C 29/16* (2006.01)
(52) U.S. Cl.
USPC ............ 568/882; 568/862; 568/883; 568/909
(58) Field of Classification Search
USPC .......................................... 568/882, 883, 909
See application file for complete search history.

(56) References Cited

U.S. PATENT DOCUMENTS

| | | | |
|---|---|---|---|
| 2,678,952 | A | 5/1954 | Krebs et al. |
| 2,813,911 | A | 11/1957 | Mason et al. |
| 4,590,314 | A | 5/1986 | Kinkade |
| 4,661,525 | A | 4/1987 | Grazioso et al. |
| 5,030,774 | A | 7/1991 | Oswald et al. |
| 5,082,977 | A | 1/1992 | Chaung |
| 5,306,848 | A | 4/1994 | Vargas |
| 5,399,793 | A | 3/1995 | Vargas et al. |
| 5,675,041 | A | 10/1997 | Kiss et al. |
| 6,049,011 | A | 4/2000 | Kiss et al. |
| 6,162,350 | A | 12/2000 | Soled et al. |
| 6,265,619 | B1 | 7/2001 | de Rijke |
| 6,278,030 | B1 | 8/2001 | Vargas et al. |
| 6,582,590 | B1 | 6/2003 | Riley et al. |
| 6,620,313 | B1 | 9/2003 | Demmin et al. |
| 6,712,955 | B1 | 3/2004 | Hou et al. |
| 6,755,963 | B2 | 6/2004 | Haluska et al. |
| 6,758,963 | B1 | 7/2004 | Hantzer et al. |
| 6,777,579 | B2 | 8/2004 | Arnoldy et al. |
| 6,783,663 | B1 | 8/2004 | Riley et al. |
| 6,863,803 | B1 | 3/2005 | Riley et al. |
| 6,929,738 | B1 | 8/2005 | Riley et al. |
| 7,229,548 | B2 | 6/2007 | Riley et al. |
| 7,232,515 | B1 | 6/2007 | Demmin et al. |
| 7,288,182 | B1 | 10/2007 | Soled et al. |
| 7,513,989 | B1 | 4/2009 | Soled et al. |

FOREIGN PATENT DOCUMENTS

| | | |
|---|---|---|
| DE | 240005 A1 | 10/1986 |
| DE | 240006 A1 | 10/1986 |
| EP | 225143 A2 | 6/1987 |

OTHER PUBLICATIONS

Balakos et al., "Effect of absorbed sulfur on heterogeneous hydroformylation over rhodium, nickel and ruthenium catalysts", Studies in Surface Science and Catalysis (1991), vol. 68, pp. 549-556.
Barrault et al., "Synthesis of higher alcohols from syngas over nickel-molybdenum catalysts, effect of methanol or ethylene", Studies in Surface Science and Catalysis (1991), vol. 61, pp. 349-355.
Green, Ind. Eng. Chem. Res. 1993,32, 1030-1034 Methane POx combined with hydroformylation to propanal.
Hedrick., in "Activity and selectivity of Group VIII, alkali-promoted Mn-Ni and Mo-based catalysts for C2+ oxygenate synthesis from the CO hydrogenation and CO/H2/C2H4 reactions", Catalysis Today, vol. 55 (2000), pp. 247-257.
Lange, Applied Catalysis A: General 283 (2005) 243-253 Oxycracking processes, ref. to hydroformylation.
Li et al.: "NiADM, a high activity and selectivity to C2+OH catalyst for catalytic conversion of synthesis gas to C1-C5 mixed alcohols", Topics in Catalysis vol. 32 No. 3-4 2005 p. 233-239.
Llorca et al., "Selective synthesis of alcohols from syngas and hydroformylation of ethylene over supported cluster-derived cobalt catalysts", Catalysis Letters 42 (1996), pp. 87-91.
Tominaga, Rutheniuim complex-catalyszed hydroformylation of alkenes with carbon dioxide, Catalysis Communications 1 (2000), pp. 1-3.
Tomishige et al. "Promoting effect of Mo on alcohol formation in hydroformylation of propylene and ethylene on Mo-Rh/SiO2", Catalysis Letters (2005), vol. 103 (1-2), pp. 15-21.
Vit et al., "Hydroformylation of ethylene over cobalt, nickel, molybdenum, CoMo and NiMo alumina supported catalysts", Applied Catalysis A: General, vol. 116 (1994), pp. 259-268.
Wang et al., "Reaction network of aldehyde hydrogenation over sulfide Ni-Mo/Al2O3 catalysts", Journal of Catalysis vol. 231 No. 1 2005 p. 20-32.
Yamagishi et al., "Selective formation of 1-propanol via ethylene hydroformylation over the catalyst originated from RhVO4", Catalyst Communications, vol. 6 (2005), pp. 421-425.
Zhang, Catalysis Letters, Simultaneous Production of Syngas and Ethylene from Methane by Combining its Catalytic Oxidative Coupling, 2006, vol. 106, Nos. 3-4, p. 161-165.
PCT/US2010/055111 International Search Report and Written Opinion.
PCT/US2010/055111 International Preliminary Report on Patentability.

*Primary Examiner* — Elvis O Price

(57) ABSTRACT

Convert an alkylene to a product stream that comprises an alkanol by subjecting a gaseous combination of a) an alkylene selected from ethylene, propylene or a combination thereof, b) carbon monoxide, c) hydrogen and, optionally, d) at least one hydrocarbon or gas diluent other than ethylene or propylene to reductive hydroformylation conditions in combination with a solid phase, sulfided, heterogeneous catalyst.

13 Claims, No Drawings ing selective reaction of a $C_n$ olefin to form a $C_{n+1}$ alcohol.

REDUCTIVE HYDROFORMYLATION OF AN ALKYLENE TO AN ALKANOL

This application is a non-provisional application claiming priority from the U.S. Provisional Patent Application No. 61/260,119, filed on Nov. 11, 2009, entitled "REDUCTIVE HYDROFORMYLATION OF AN ALKYLENE TO AN ALKANOL," the teachings of which are incorporated by reference herein, as if reproduced in full hereinbelow.

This application relates to a method of converting an alkylene such as ethylene, propylene or a mixture thereof to, respectively, propanol and a mixture of butanols. The method includes use of reductive hydroformylation conditions and a solid phase, sulfided, heterogeneous catalyst.

U.S. Pat. No. 4,590,314 (Kinkade) discloses a selective reaction of a $C_n$ olefin with carbon monoxide (CO) and hydrogen ($H_2$) in the presence of a catalyst consisting essentially of molybdenum sulfide and an alkali metal or alkaline earth metal compound to form a $C_{n+1}$ alcohol. "n" is a positive integer greater than or equal ($\geq$) 2.

U.S. Pat. No. 5,675,041 (Kiss et al.) relates to production of aldehydes by hydroformylating a mixture containing olefins with two to five carbon atoms ($C_2$ to $C_5$). See also U.S. Pat. No. 6,049,011 (Kiss et al.) for hydroformylation of a dilute ethylene-containing stream using a rhodium-containing catalyst to yield propanal.

U.S. Pat. No. 5,082,977 (Chaung)) focuses on use of a solid phase catalyst consisting essentially of one or more sulfided Group VIII metals to react olefins (e.g. ethylene or propylene) with CO and $H_2$ to produce aldehydes. The catalyst is represented by a formula $A_xMS_yMn_z$ where A is an alkali metal, M is a Group VIII metal, S is sulfur, Mn is manganese, x and z are in a range of 0 to 10 and y is in a range of from 0.01 to 2. The catalyst may be used with or without a support such as alumina or silica.

U.S. Pat. No. 6,777,579 (Arnoldy et al.) discusses a hydroformylation process that involves reacting a compound having at least one olefinic carbon-to-carbon bond with $H_2$ and CO in the presence of a cobalt catalyst and a sulfur-containing additive such as an alkali metal sulfide.

U.S. Pat. No. 4,661,525 (Grazioso et al.) teaches a process for producing a mixture of lower ($C_2$ to $C_6$) alcohols by contacting synthesis gas or syngas (a mixture of CO and $H_2$) with a supported catalyst consisting essentially of molybdenum, a metal selected from cobalt, iron and nickel, and an alkali metal promoter selected from potassium, cesium and rubidium. Suitable supports include alumina and silica.

Vit et al., in "Hydroformylation of ethylene over cobalt, nickel, molybdenum, CoMo and NiMo alumina supported catalysts", *Applied Catalysis A: General*, volume 116 (1994), pages 259-268, provides teachings about vapor phase hydroformylation of ethylene at temperatures of 513 Kelvin to 563 Kelvin, 10 to $10^5$ pascals overall pressure in the presence of hydrogen sulfide ($H_2S$) in the feed. Vit et al. suggests that cobalt and nickel catalysts provide the best hydroformylation activity and that addition of molybdenum enhances formation of ethane and sulfur compounds but decreases the hydroformylation reaction.

S. A. Hedrick et al., in "Activity and selectivity of Group VIII, alkali-promoted Mn—Ni and Mo-based catalysts for C2+ oxygenate synthesis from the CO hydrogenation and CO/$H_2$/$C_2H_4$ reactions", *Catalysis Today*, volume 55 (2000), pages 247-257 disclose, in part, $H_2S$-treated Group VIII metal catalysts, alkali-promoted Mn—Ni catalysts and Mo-based catalysts in ethylene hydroformylation reactions. Table 1 discloses an alkali-molybdenum sulfide catalyst. Table 2 discloses a sulfided nickel-potassium-molybdenum catalyst on a silica support (catalyst IV-3). Table 4 shows no production of alkanols and some production of C3+ hydrocarbons and $C_2H_5$CHO with catalyst IV-3 in a hydroformylation reaction.

Yamagishi et al., in "Selective formation of 1-propanol via ethylene hydroformylation over the catalyst originated from $RhVO_4$", *Catalyst Communications*, volume 6 (2005), pages 421-425, discuss performance of vanadia-modified rhodium/silica catalysts in hydroformylation of ethylene to propanol. They suggest that performance depends on calcination temperature and formation of $RhVO_4$ mixed oxide crystallites.

U.S. Pat. No. 2,813,911 ((Mason et al.) teaches preparation of oxygenated organic compounds by reacting CO and $H_2$ with carbon compounds containing olefinic linkages in the presence of a carbonylation catalyst (e.g. a salt of a catalytically active metal such as cobalt with a high molecular weight acid such as stearic acid) to form an aldehyde and then hydrogenating the aldehyde with a hydrogenation catalyst to form an oxygenated organic compound such as an alcohol. The hydrogenation catalyst comprises molybdenum sulfide on an active carbon carrier. This two stage preparation is frequently referred to as an "oxo alcohol process" or simply as an "oxo process".

U.S. Pat. No. 2,678,952 (Krebs) discloses a carbonylation process wherein olefins, CO and $H_2$ are contacted in an initial carbonylation zone with a cobalt carbonylation catalyst to produce an aldehyde product and the aldehyde product is subjected to hydrogenation in a hydrogenation zone in the presence of a sulfactive hydrogenation catalyst such as molybdenum sulfide on activated carbon. Known hydrogenation catalysts also include nickel and tungsten in their oxide or sulfide form, whether supported or not.

U.S. Pat. No. 5,306,848 (Vargas) provides teachings related to the oxo process including a reference to prior patents such as U.S. Pat. No. 5,030,774 about using sulfided bimetallic cobalt and molybdenum oxides or nickel and molybdenum oxides supported on alumina as a hydrogenation catalyst. Vargas focuses on trimetallic nickel, cobalt and molybdenum catalysts in the form of oxides of those metals and supported on either alumina or silica alumina. Vargas prefers use of such catalysts in their sulfided form. See also U.S. Pat. No. 5,399,793 (Vargas et al.).

K. Tominaga et al., in "Ruthenium complex-catalyzed hydroformylation of alkenes with carbon dioxide", *Catalysis Communications* 1 (2000), pages 1-3, note that carbon dioxide ($CO_2$) can be used as a reactant for hydroformylation of alkenes. They suggest that $CO_2$ transforms to CO via hydrogenation, e.g. by use of a ruthenium cluster complex in the presence of a halide salt.

J. Llorca et al., in "Selective synthesis of alcohols from syngas and hydroformylation of ethylene over supported cluster-derived cobalt catalysts", *Catalysis Letters* 42 (1996), pages 87-91, teach use of supported cobalt catalysts prepared from reaction of $Co_2(CO)_8$ with magnesium oxide (MgO), zinc oxide (ZnO) and lanthanum oxide ($La_2O_3$) surfaces. They test catalytic activity with a 1:1:1 mixture of ethylene ($C_2H_4$), carbon monoxide (CO) and hydrogen ($H_2$).

U.S. Pat. No. 6,777,579 (Arnoldy et al.) relates to a hydroformylation process that involves reacting a compound having at least one olefinic carbon-to-carbon bond with $H_2$ and CO in the presence of a cobalt catalyst (e.g. those that contain an organic tertiary phosphine ligand) and a sulfur-containing additive (e.g. an alkali metal or alkaline earth metal sulfide) that suppresses formation of cobalt carbide.

J Barrault et al., in "Synthesis of higher alcohols from syngas over nickel-molybdenum catalysts, effect of methanol or ethylene", *Studies in Surface Science and Catalysis*

(1991), volume 61, pages 349-355, discuss bimetallic nickel-molybdenum catalysts promoted with potassium supported on manganese oxide ($MnO_2$) or zinc oxide (ZnO) in production of alcohols via hydroformylation.

M. Balakos et al., in "Effect of absorbed sulfur on heterogeneous hydroformylation over rhodium, nickel and ruthenium catalysts", *Studies in Surface Science and Catalysis* (1991), volume 68, pages 549-556, note that absorbed sulfur slightly enhances ethylene hydroformylation on $Rh/SiO_2$ and $Ni/SiO_2$ catalysts.

East German Patent (DD) 240005 (Stoss et al.) presents teachings about preparation of alcohols, especially $C_3$ to $C_5$ alcohols, by hydroformylating olefins in the presence of a sulfided cobalt-containing catalyst. The teachings suggest that a low carbon dioxide ($CO_2$) content (less than 1 volume percent) synthesis gas stream gives a higher alcohol content than a higher $CO_2$ content (4.1 volume percent) synthesis gas stream.

DD 240006 (Stoss et al.) builds upon DD 240005 and teaches that continuous addition of an amount of liquid methanol provides an increase in both space time yield of alcohols such as propanol and useful catalyst (sulfided cobalt) life.

Tomishige et al., in "Promoting effect of Mo on alcohol formation in hydroformylation of propylene and ethylene on Mo—$Rh/SiO_2$", Catalysis Letters (2005), volume 103 (1-2), pages 15-21, note that addition of Mo to $Rh/SiO_2$ catalysts promotes alcohol formation in hydroformylation of propylene and ethylene.

U.S. Pat. No. 6,278,030 (Vargas et al.) relates to preparing alcohols by the oxo process, especially characterized by use of bulk multimetallic hydrogenation catalysts that comprise at least one Group VIII non-noble metal (e.g. nickel, cobalt or a mixture of the two) and at least two Group VIB metals (e.g. molybdenum and tungsten). The process also involves use of a rhodium-containing hydroformylation catalyst. See also related case family members U.S. Pat. No. 6,712,955 (Hou et al.), U.S. Pat. No. 6,929,738 (Riley et al.), U.S. Pat. No. 6,620,313 (Demmin et al.), U.S. Pat. No. 6,582,590 (Riley et al.), U.S. Pat. No. 7,232,515 (Demmin et al.), U.S. Pat. No. 6,863,803 (Riley et al.), U.S. Pat. No. 7,513,989 (Soled et al.), U.S. Pat. No. 6,162,350 (Soled et al.), U.S. Pat. No. 6,783,663 (Riley et al.), U.S. Pat. No. 7,288,182 (Soled et al.), U.S. Pat. No. 6,278,030 (Vargas et al.), U.S. Pat. No. 6,758,963 (Hantzer et al.), U.S. Pat. No. 7,229,548 (Riley et al.) and U.S. Pat. No. 6,755,963 (Haluska et al.).

In some aspects, this invention is a method for converting an alkylene to a product stream that comprises an alkanol, the method comprising subjecting a gaseous combination of a) an alkylene selected from ethylene, propylene or a combination thereof, b) carbon monoxide, c) hydrogen and, optionally, d) at least one hydrocarbon or gas diluent other than ethylene or propylene to reductive hydroformylation conditions in combination with a solid phase, sulfided, heterogeneous catalyst, such combination being sufficient to convert ethylene to propanol and propylene to butanol, said catalyst comprising at least one Group VIII metal, at least one Group VI metal, at least one alkali metal and sulfur.

The Group VIII metal may be any one or more of iron, cobalt, nickel, ruthenium, rhodium, palladium, osmium, iridium and platinum, preferred results follow with one or more of iron, cobalt, and nickel or a combination of two or more of iron, cobalt and nickel.

The Group VI metal may be any one or more of chromium, molybdenum and tungsten, but preferred results follow with molybdenum.

The alkali metal may be any of lithium, sodium, potassium, rubidium and cesium, but either or both of potassium and cesium yields preferred results.

The catalyst may, if desired, be supported on a catalyst support. Suitable catalyst supports include those selected from a group consisting of silica, titania, zirconia, zinc oxide, magnesium oxide, lanthanum oxide, manganese oxide, activated carbon, and hydrotalcite (clays).

"Reductive hydroformylation" means a reaction or process of producing an alcohol from an olefin or alkylene, carbon monoxide (CO) and two equivalents of hydrogen ($H_2$) gas, typically in the presence of a catalyst.

Reductive hydroformylation conditions comprise a reaction temperature of from 200 degrees centigrade (° C.) to 400° C. and a reaction pressure of from 100 pounds per square inch gauge (psig) (689.5 kilopascals (kPa)) to 3000 psig (20.7 megapascals (MPa)). Reductive hydroformylation conditions may further comprise a gaseous combination gas hourly space velocity of from 1000 $hr^{-1}$ to 15,000 $hr^{-1}$.

The gaseous combination comprises, consists essentially of or consists of a) an alkylene selected from ethylene, propylene or a combination thereof, b) carbon monoxide and c) hydrogen. The gaseous combination may further comprise, consist essentially of, or consist of one or more of carbon dioxide and methanol. Carbon dioxide, methanol or both carbon dioxide and methanol may be used as a source of CO. The gaseous combination may still further comprise, consist essentially or consist of a sulfiding agent selected from a group consisting of hydrogen sulfide, an alkyl mercaptan, a dialkyl sulfide or a dialkyl disulfide. The gaseous combination optionally includes at least one hydrocarbon or gas diluent other than ethylene or propylene.

The alkylene is selected from ethylene, propylene or a mixture thereof and the reductive hydroformylation conditions convert at least a portion of ethylene to propanol and at least a portion of propylene to a butanol. In converting ethylene to propanol, one may also obtain an amount of propionaldehyde. If desired, convert at least a portion of the propionaldehyde to propanol by one or more of additional time of exposure to the catalyst or exposure to a second stage hydrogenation catalyst. In converting propylene to butanol, one may also obtain an amount of butryaldehyde. If desired, convert at least a portion of the butyraldehyde to butanol by one or more of additional time of exposure to the catalyst or exposure to a second stage hydrogenation catalyst.

Second stage hydrogenation catalysts include those selected from a group consisting of palladium (Pd), nickel (Ni), copper (Cu), chromium (Cr), iron (Fe), zinc (Zn), silver (Ag), gallium (Ga), tin (Sn), cobalt-molybdenum sulfide (CoMoSx), nickel-molybdenum sulfide (NiMoSx), and iron-molybdenum sulfide (FeMoSx). Other suitable second stage hydrogenation catalysts include those based on copper chromite, copper zinc oxide and/or supported nickel.

The catalyst may be present as a slurry of catalyst particles in a non-reactive fluid selected from a group consisting of paraffin solvents, non-paraffin alkane solvents, and oxygenate solvents including products of the method described and claimed herein.

EXAMPLE (EX) 1

Preparation of Alkali Metal-Modified Cobalt/Nickel-Molybdenum Sulfide Catalyst

Charge a 1 liter (L) Erlenmeyer flask with 38 milliliters (mL) of glacial acetic acid and 64 mL of deionized water, and then heat flask contents to 60° C. In a 150 mL beaker, dissolve 3.98 grams (g) (13.7 millimoles (mmol)) cobalt (II) nitrate hexahydrate ($Co(NO_3)_2 \cdot 6H_2O$) and 3.40 g (13.7 mmol) nickel acetate tetrahydrate ($Ni(CH_3CO_2)_2 \cdot 4H_2O$) in 64 mL of deionized water. In a 500 mL beaker, dissolve 9.6 g (7.8 mmol) of ammonium molybdate(VI) tetrahydrate (($NH_4)_6 Mo_7O_{24} \cdot 4H_2O$) in approximately 40 mL of deionized water, heat the beaker contents to 65° C., then add approximately 40 g of 20% ammonium sulfide (($NH_4)_2S$) and heat the beaker contents, with stirring for 30 minutes, to a temperature of 65° C., resulting in a homogeneous, dark red solution. Co-feed aliquots of solutions from the two beakers to the acetic acid solution at equal rates over a 30 minute period. The reaction is immediate, yielding a fine black precipitate. Following addition of the beaker contents, maintain contents of the flask (a suspension of the black precipitate in liquid components of the flask) at a temperature of 65° C., with vigorous stirring (at a rate of approximately 800 revolutions per minute (rpm)) for 30 minutes, before allowing contents of the flask to cool to ambient temperature (nominally 25° C.). Centrifuge the flask contents for 20 minutes at 2800 rpm to yield a heavy black cake and a light blue-green supernatant. Decant the supernatant from the cake. Suspend cake solids in approximately 250 mL of water, then separate the solids via filtration and dry the solids in air at 70° C. for 18 hours.

Reduce the dried solids using a tube furnace and ultra-high purity argon (Ar) (99.999% pure). Add the solids to the furnace, purge the furnace for 30 minutes with Ar flowing at a rate of 50 standard cubic centimeters per minute (scc/min), then heat the furnace contents to a set point temperature of 500° C., maintain that temperature for one hour, then allow the contents to cool to ambient temperature over a period of 18 hours.

Use a ceramic mortar and pestle to prepare a catalyst compound (dark grey powder) that contains 10 percent by weight (wt %) alkali carbonate and 90 wt % of the reduced, dried solids, each wt % being based upon combined weight of alkali carbonate and reduced, dried solids. Store the catalyst compound under nitrogen.

Evaluate the catalyst compound, which has a sulfur to molybdenum (S:Mo) ratio of approximately 2:1, for conversion of an alkylene and synthesis gas to an alkanol using a 23 inch (58.4 centimeter (cm)) by ¼ inch (0.6 cm) tubular, stainless steel reactor. Fit the bottom of the reactor with a 2 micrometer (μm) snubber gasket via a metal gasket face seal fitting connection. Charge the reactor, in order, with a layer of glass beads weighing 3 grams (g) and having a thickness (measured from the bottom of the reactor) of approximately 5.5 inches (14 centimeters (cm)), a layer of quartz wool having a thickness of 0.125 inches (0.32 cm), 1.5 g of the catalyst compound, a layer of quartz wool having a thickness of 0.125 inches (0.32 cm), and a layer of glass beads weighing 7-8 g and having a thickness of 14-15 inches (35.6 cm to 38.1 cm). Fit the reactor top with a 5 μm snubber gasket via a VCR® (Swagelok) connection. Connect the reactor to the rest of the system via the feed line at the top and the exit-gas line at the bottom of the reactor tube, then pressure test the reactor overnight with nitrogen at a pressure of 1700 psig (11.7 MPa).

Use a pre-mixed gas mixture that contains, on a mole percent basis, 45 parts CO, 45 parts $H_2$, 5 parts $N_2$ and 5 parts alkylene as a feedstream. For this Ex 1, the alkali carbonate is potassium carbonate ($K_2CO_3$), the alkylene is propylene and the alkanol is a mixture of butanols. Conduct catalyst testing with the catalyst and feedstream at a pressure of 1500 psi (10.3 MPa) and temperatures of 300° C. and 320° C. Use online gas chromatography to analyze product from the reactor. Summarize analytical results in Table 1 below. Determine percent conversion by gas chromatograph analysis (GCA). Calculate percent selectivity, on a total carbon percent basis, by GCA. "Other", in Table 1, represents esters, hydrocarbons having a chain length of 5 or more carbons, and waxes. Show productivity as pounds of product alkanol (1-butanol and isobutanol in this Ex) per square foot of catalyst per hour (grams of product per gram of catalyst per hour).

EX 2

Preparation of Alkali Metal-Modified Cobalt-Molybdenum Sulfide Catalyst

Replicate Ex 1, but eliminate addition of the $Ni(CH_3 CO_2)_2 \cdot 4H_2O$, add a total charge of $Co(NO_3)_2 \cdot 6H_2O$ of 7.95 g (27.32 mmoles), and 10 wt. % of $K_2CO_3$ (relative to the $CoMoS_x$).

COMPARATIVE EXAMPLE (CEX) 3

Preparation of Cobalt-Molybdenum Sulfide Catalyst

Replicate Ex 2, but eliminate addition of $K_2CO_3$.

TABLE 1

| Ex/CEx//Measure | 1 | 2 | 3 | 1 | 2 | 3 |
|---|---|---|---|---|---|---|
| Temperature (° C.) | 300 | 300 | 300 | 320 | 320 | 320 |
| Percent Conversion | | | | | | |
| Hydrogen | 16.0 | 15.0 | 24.0 | 16.0 | 22.0 | 20.0 |
| Carbon monoxide | 12.0 | 11.0 | 11.0 | 12.0 | 16.0 | 6.0 |
| Propylene | 25.0 | 23.0 | 20.3 | 18.0 | 25.0 | 10.0 |
| Percent Selectivity | | | | | | |
| 1-butanol | 25.0 | 31.0 | 0.0 | 20.0 | 24.0 | 0.0 |
| Iso-butanol | 12.0 | 13.0 | 0.0 | 10.0 | 10.0 | 0.0 |
| Butane | 6.0 | 7.0 | 11.0 | 4.0 | 4.0 | 9.0 |
| Carbon dioxide | 12.0 | 12.0 | 2.0 | 15.0 | 15.0 | 4.0 |
| Methanol | 7.0 | 11.0 | 1.0 | 8.0 | 11.0 | 1.0 |
| Ethanol | 1.0 | 7.0 | 0.0 | 7.0 | 10.0 | 0.0 |
| Propanol | 0.0 | 1.0 | 2.0 | 3.0 | 7.0 | 1.0 |
| Methane | 3.0 | 2.0 | 1.0 | 5.0 | 3.0 | 2.0 |
| Ethane | 1.0 | 1.0 | 2.0 | 1.0 | 1.0 | 3.0 |
| Propane | 24.5 | 15.0 | 80.0 | 15.0 | 15.0 | 79.0 |
| Other | 8.5 | 0.0 | 1.0 | 12.0 | 0.0 | 1.0 |
| Productivity (butanols) | 1.21 | 7.88 | 0.0 | 5.46 | 10.30 | 0.0 |

The data in Table 1 show the reductive hydroformylation of propylene to butanols, and demonstrate the beneficial effect of modifying the catalyst with alkali (potassium).

CEX 4

Preparation of Molybdenum Sulfide Catalyst

Reduce commercial ammonium tetrathiomolybdate $(NH_4)_2 MoS_4$ using a tube furnace, procedure and ultra-high purity argon (Ar) (99.999% pure) as in Ex 1. See Tables 2 and 3 below for analytical results data.

EX 5

Preparation of Potassium-Modified Molybdenum Sulfide Catalyst

Replicate Ex 2, but use ethylene as the alkylene and eliminate addition of $Co(NO_3)_2 \cdot 6H_2O$. See Tables 2 and 3 below for analytical results data.

A comparison of this example to CEx 4 shows the beneficial effect of alkali modification of the catalyst to control product selectivity toward propanol.

CEX 6

Cobalt-Molybdenum Sulfide Catalyst

Replicate CEx 3, but use ethylene as the alkylene. See Tables 2 and 3 for analytical results data.

EX 7

Potassium-Modified Cobalt-Molybdenum Sulfide Catalyst

Replicate Ex 2, but use ethylene as the alkylene. See Tables 2 and 3 for analytical results data.

The data presented in Tables 2 and 3, specifically for CEx 6 and this Ex 7, demonstrates that modification of the CoMoSx catalyst with potassium enhances the selectivity for propanol production when used for the reductive hydroformylation of ethylene.

EX 8

Lithium-Modified Cobalt-Molybdenum Sulfide Catalyst

Replicate Ex 7, but substitute 10 wt. % (relative to the bulk CoMoSx) of lithium carbonate ($Li_2CO_3$) for the $K_2CO_3$. See Tables 2 and 3 for analytical results data.

The data for this Ex 8 and that for CEx 6 show that modification of the CoMoSx catalyst with lithium changes the selectivity of the system, but the catalyst is still most selective for ethane, propane, and $CO_2$.

EX 9

Sodium-Modified Cobalt-Molybdenum Sulfide Catalyst

Replicate Ex 7, but substitute potassium for 10 wt. % (relative to the bulk CoMoSx) of sodium carbonate ($Na_2CO_3$) for the $K_2CO_3$. See Tables 2 and 3 for analytical results data.

A comparison of this Ex 9 with CEx 6 demonstrates that modification of the CoMoSx catalyst with sodium enhances selectivity of the catalyst for propanol.

EX 10

Cesium-Modified Cobalt-Molybdenum Sulfide Catalyst

Replicate Ex 7, but substitute 10 wt. % (relative to the bulk CoMoSx) of cesium carbonate ($Cs_2CO_3$) for the $K_2CO_3$. See Tables 2 and 3 for analytical results data.

In Tables 2 and 3, comparison of this catalyst with CEx 6 shows that modification of the system with cesium enhances selectivity of the catalyst for the production of propanol.

EX 11

Rubidium-Modified Cobalt-Molybdenum Sulfide Catalyst

Replicate Ex 7, but substitute 10 wt. % (relative to the bulk CoMoSx) of rubidium carbonate ($Rb_2CO_3$) for the $K_2CO_3$. See Tables 2 and 3 for analytical results data.

In Tables 2 and 3, comparison of this catalyst with CEx 6 shows that modification of the system with rubidium enhances selectivity of the catalyst for the production of propanol.

EX 12

Potassium-Modified Cobalt/Nickel-Molybdenum Sulfide Catalyst

Replicate Ex 1, but use ethylene as the alkylene. See Tables 2 and 3 for analytical results data.

CEX 13

Cobalt/Nickel-Molybdenum Sulfide Catalyst

Replicate Ex 1, but do not add an alkali modifier to the catalyst. See Tables 2 and 3 for analytical results data.

A comparison of Ex 12 with CEx 13 shows that modification of the system with potassium enhances selectivity of the catalyst for production of propanol.

TABLE 2

| Ex/CEx//Measure | 4 | 5 | 6 | 7 | 8 | 9 | 10 | 11 | 12 | 13 |
|---|---|---|---|---|---|---|---|---|---|---|
| Percent Conversion | | | | | | | | | | |
| Hydrogen | 46 | 43 | 20 | 16 | 28 | 32 | 21 | 26 | 8 | 17 |
| Carbon monoxide | 25 | 35 | 6 | 9 | 13 | 28 | 13 | 18 | 4 | 7 |
| Ethylene | 100 | 79.9 | 99 | 59 | 99.9 | 100 | 86 | 99 | 26 | 100 |
| Percent Selectivity | | | | | | | | | | |
| Propanol | 0 | 45 | 1 | 48 | 3 | 27 | 48 | 32 | 39 | 0 |
| Propanal | 0 | 0 | 0 | 2 | 0 | 0 | 2 | 0 | 2 | 0 |
| Ethane | 42 | 7 | 54 | 17 | 28 | 17 | 10 | 20 | 13 | 64 |
| Carbon dioxide | 18 | 16 | 6 | 6.6 | 20 | 20 | 5 | 12 | 6 | 7 |
| Methanol | 0 | 6 | 0 | 8 | 0 | 1 | 3 | 1 | 1 | 0 |
| Ethanol | 0 | 7 | 0 | 4 | 0 | 2 | 2 | 2 | 4 | 0 |
| Butanol | 0 | 2 | 0 | 1 | 1 | 4 | 2 | 4 | 15 | 0 |
| Methane | 16 | 7 | 2 | 1 | 3 | 3 | 1 | 1 | 1 | 1 |
| Propylene | 0 | 2 | 0 | 7 | 0 | 2 | 11 | 6 | 2 | 0 |
| Propane | 19 | 2 | 28 | 2 | 33 | 19 | 16 | 18 | 1 | 22 |
| Butane | 4 | 1 | 8 | 2 | 11 | 5 | 0 | 4 | 2 | 4 |
| Other | 1 | 5 | 7 | 0.4 | 1 | 0 | 0 | 0 | 6 | 2 |
| Productivity (propanol) | 0.0 | 8.4 | 0.0 | 18.18 | 0.61 | 16.97 | 22.42 | 16.36 | 7.88 | 0.00 |

TABLE 3

| Ex/CEx//Measure | 4 | 5 | 6 | 7 | 8 | 9 | 10 | 11 | 12 | 13 |
|---|---|---|---|---|---|---|---|---|---|---|
| Percent Conversion | | | | | | | | | | |
| Hydrogen | 78 | 59 | 19 | 26 | 27 | 45 | 29 | 31 | 18 | 18 |
| Carbon monoxide | 63 | 58 | 9 | 16 | 18 | 42 | 21 | 25 | 13 | 9 |
| Ethylene | 100 | 96 | 99 | 72 | 99.9 | 100 | 96 | 100 | 39 | 100 |
| Percent Selectivity | | | | | | | | | | |
| Propanol | 0 | 21 | 1 | 44 | 1 | 7 | 40 | 5 | 30 | 0 |
| Propanal | 19 | 0 | 0 | 2 | 0 | 0 | 1 | 0 | 1 | 0 |
| Ethane | 0 | 12 | 51 | 13 | 34 | 14 | 14 | 24 | 14 | 62 |
| Carbon dioxide | 46 | 29 | 13 | 11 | 20 | 31 | 10 | 22 | 16 | 11 |
| Methanol | 0 | 1 | 0 | 9 | 1 | 2 | 3 | 1 | 12 | 0 |
| Ethanol | 0 | 4 | 0 | 8 | 0 | 2 | 3 | 2 | 9 | 0 |
| Butanol | 0 | 0 | 0 | 1 | 1 | 2 | 3 | 4 | 2 | 0 |
| Methane | 30.0 | 13 | 2 | 3 | 3 | 4 | 3 | 1 | 6 | 3 |
| Propylene | 0 | 5 | 0 | 5 | 0 | 0 | 11 | 0 | 2 | 0 |
| Propane | 2 | 7 | 24 | 1 | 40 | 19 | 4 | 23 | 2 | 20 |
| Butane | 1 | 2 | 5 | 2 | 0 | 12 | 2 | 10 | 3 | 3 |
| Other | 0 | 6 | 4 | 1 | 0 | 7 | 6 | 8 | 3 | 1 |
| Productivity (propanol) | 0.0 | 21.6 | 0.61 | 25.46 | 0.61 | 6.06 | 23.64 | 3.03 | 7.27 | 0.00 |

The data presented in Tables 2 and 3 demonstrate the beneficial effect of modification of the $CoMoS_x$, $Co/NiMoS_x$ catalyst with alkali for the reductive hydroformylation of ethylene at 300° C. and 320° C., respectively.

CEX 14

Nickel-Molybdenum Sulfide Catalyst

Replicate Ex 1, but use ethylene as the alkylene, eliminate $Co(NO_3)_2.6H_2O$ and add a total charge of the $Ni(CH_3CO_2)_2.4H_2O$ of 6.80 grams, and eliminate the potassium carbonate. See Table 4 for analytical results data.

EX 15

Potassium-Modified Nickel-Molybdenum Sulfide Catalyst

Replicate CEx 14, but do not eliminate the potassium carbonate. See Table 4 for analytical results data.

EX 16

Cesium-Modified Nickel-Molybdenum Sulfide Catalyst

Replicate Ex 15, but use cesium carbonate rather than potassium carbonate. See Table 4 for analytical results data.

The data in Table 4 show that modification of the NiMoSx catalyst with potassium (Ex 15) or cesium (Ex 16) beneficially affects selectivity of the catalyst toward propanol at 300° C. and 320° C.

TABLE 4

| Ex/CEx//Measure | 14 | 15 | 16 | 14 | 15 | 16 |
|---|---|---|---|---|---|---|
| Temperature (° C.) | 300 | 300 | 300 | 320 | 320 | 320 |
| Percent Conversion | | | | | | |
| Hydrogen | 17 | 14 | 18 | 18 | 16 | 23 |
| Carbon monoxide | 9 | 9 | 13 | 10 | 11 | 17 |
| Ethylene | 100 | 45 | 53 | 100 | 50 | 69 |

TABLE 4-continued

| Ex/CEx//Measure | 14 | 15 | 16 | 14 | 15 | 16 |
|---|---|---|---|---|---|---|
| Percent Selectivity | | | | | | |
| Propanol | 1 | 25 | 60 | 1 | 25 | 58 |
| Propanal | 0 | 1 | 0 | 1 | 1 | 1 |
| Ethane | 51 | 22 | 11 | 55 | 27 | 9 |
| Carbon dioxide | 16 | 10 | 8 | 16 | 15 | 10 |
| Methanol | 0 | 5 | 5 | 0 | 5 | 4 |
| Ethanol | 0 | 4 | 4 | 0 | 5 | 4 |
| Butanol | 0 | 3 | 3 | 0 | 3 | 4 |
| Methane | 2 | 2 | 2 | 3 | 4 | 3 |
| Propylene | 0 | 4 | 2 | 0 | 5 | 3 |
| Propane | 20 | 3 | 1 | 20 | 5 | 2 |
| Butane | 7 | 2 | 2 | 5 | 5 | 1 |
| Other | 3 | 5 | 1 | 0 | 0 | 1 |
| Productivity (propanol) | 0.61 | 8.48 | 13.33 | 0.0 | 7.56 | 18.79 |

CEX 17

Magnesium-Modified Nickel-Molybdenum Sulfide Catalyst

Replicate Ex 7, but use magnesium carbonate in place of potassium carbonate. See Table 5 below for analytical results data. Table 5 also includes data from CEx 6 for ease of comparison.

CEX 18

Barium-Modified Nickel-Molybdenum Sulfide Catalyst

Replicate CEx 17, but use barium carbonate rather than magnesium carbonate. See Table 5 below for analytical results data.

The data in Table 6 show that alkaline earth modification of the CoMoSx catalyst with magnesium (CEx 17) or barium (CEx 18) does not have a significant effect upon the nickel-molybdenum catalyst at the conditions studied for selectivity to propanol.

TABLE 5

| Ex/CEx//Measure | 6 | 17 | 18 | 6 | 17 | 18 |
|---|---|---|---|---|---|---|
| Temperature (° C.) | 300 | 300 | 300 | 320 | 320 | 320 |
| Percent Conversion | | | | | | |
| Hydrogen | 20 | 16 | 19 | 19 | 17 | 18 |
| Carbon monoxide | 6 | 3.5 | 5 | 9 | 4 | 8 |
| Ethylene | 99.8 | 99 | 99.9% | 99 | 100 | 99.9% |
| Percent Selectivity | | | | | | |
| Propanol | 1 | 3 | 1 | 1 | 1 | 0 |
| Propanal | 0 | 0 | 0 | 0 | 1 | 0 |
| Ethane | 54 | 55 | 53 | 51 | 61 | 54.5 |
| Carbon dioxide | 6 | 1 | 3 | 13 | 6.5 | 13.5 |
| Methanol | 0 | 0 | 0 | 0 | 0 | 0 |
| Ethanol | 0 | 0 | 0 | 0 | 0 | 0 |
| Butanol | 0 | 1 | 0 | 0 | 0 | 0 |
| Methane | 2 | 0 | 0 | 2 | 1 | 2 |
| Propylene | 0 | 4 | 0 | 0 | 0 | 0 |
| Propane | 28 | 27 | 32 | 24 | 25 | 24 |
| Butane | 8 | 7 | 8 | 5 | 4 | 5 |
| Other | 1 | 2 | 3 | 4 | 0.5 | 1 |
| Productivity (propanol) | 0.0 | 0.61 | 0.0 | 0.61 | 0.0 | 0.0 |

EX 19-30

Alkali Metal-Modified Cobalt/Molybdenum Sulfide Catalysts

Replicate Ex 1, but change the alkylene to ethylene, and use 5 wt %, 10 wt % and 20 wt % of lithium (Li) (respectively Ex 19, 20 and 21), sodium (Na) (respectively Ex 22, 23 and 24), potassium (K) (respectively Ex 25, 26 and 27) or cesium (Cs) (respectively Ex 28, 29 and 30). See Table 6 below for analytical results data.

The data presented in Table 6 show the effect of varying loadings of alkali on the CoMoSx catalyst for the reductive hydroformylation of ethylene at 300 deg Celsius. The data also show that selectivity to reaction products can be tuned by varying the amount of alkali modifier used to prepare the catalyst.

EX 31-32

Reductive Hydroformylation of Ethylene Using Slurried Catalysts

Charge a 300 mL stirred tank reactor (equipped with a gas-dispersing impeller spinning at 1300 rpm) with 150 mL of hexadecane solvent (Alfa Aesar #A10322, 99%) and 7.5 g of metal-sulfide catalyst in powder form (cobalt-molybdenum sulfide for Ex 31 and cobalt/nickel-molybdenum sulfide for Ex 32). Heat the system to 275° C. under a helium blanket pressure of 10 psig (68.9 KPa). Pressurize the reactor to 1450 psig (10 MPa) using a pre-mixed gas cylinder containing, on a mole percent basis: 15% ethylene, 40% $H_2$, 40% CO, 5% $N_2$, and 50 parts per million by weight of combined weight of ethylene, $H_2$, CO and $N_2$, (ppm) hydrogen sulfide. Add make-up gas from the cylinder to the reactor as needed to maintain reactor pressure at 1450 psig (10 MPa). Collect gas and liquid samples each hour for five hours and analyze the samples by gas chromatography. See Table 7 for experimental results including ethylene conversion, product selectivity and productivity. Terminal olefins contained in the solvent, as impurities or products of a background cracking reaction, are hydroformylated and account for up to 10% of the conversion of the CO.

TABLE 6

| Ex/CEx//Measure | 19 | 20 | 21 | 22 | 23 | 24 | 24 | 26 | 27 | 28 | 29 | 30 |
|---|---|---|---|---|---|---|---|---|---|---|---|---|
| Percent Conversion | | | | | | | | | | | | |
| Hydrogen | 23 | 28 | 31 | 32 | 32 | 21 | 28 | 16 | 15 | 21 | 22 | 16 |
| Carbon monoxide | 9 | 13 | 27 | 26 | 28 | 14 | 20 | 9 | 11 | 13 | 14 | 11 |
| Ethylene | 99.9 | 99.9 | 99.9 | 99.0 | 100.0 | 54 | 97.0 | 59.0 | 18 | 86 | 60.8 | 41.1 |
| Percent Selectivity | | | | | | | | | | | | |
| Propanol | 1 | 3 | 3 | 50 | 27 | 66 | 61 | 48 | 37 | 48 | 67 | 69 |
| Propanal | 0 | 0 | 0 | 0 | 0 | 1 | 1 | 2 | 3 | 2 | 1 | 1 |
| Ethane | 46 | 28 | 20 | 4 | 17 | 5 | 5 | 17 | 4 | 10 | 4 | 3 |
| Carbon dioxide | 7 | 20 | 24 | 11 | 20 | 6 | 7 | 6.6 | 12 | 5 | 6 | 6 |
| Methanol | 1 | 0 | 0.4 | 3 | 1 | 7 | 4 | 8 | 18 | 3 | 8 | 9 |
| Ethanol | 0 | 0 | 0 | 2 | 2 | 6 | 2 | 4 | 11 | 2 | 5 | 6 |
| Butanol | 0 | 1 | 1 | 4 | 4 | 1 | 3 | 1 | 0 | 2 | 1 | 0 |
| Methane | 1 | 3 | 3 | 1 | 3 | 1 | 1 | 1 | 5 | 1 | 2 | 2 |
| Propylene | 0 | 0 | 0 | 9 | 2 | 1 | 8 | 7 | 0 | 11 | 1 | 0 |
| Propane | 33 | 33 | 31 | 5 | 19 | 0 | 2 | 2 | 0 | 16 | 0 | 0 |
| Butane | 8 | 11 | 10 | 2 | 5 | 1 | 1 | 2 | 0 | 0 | 0 | 0 |
| Other | 3 | 1 | 7.6 | 9 | 0 | 5 | 5 | 0.4 | 10 | 0 | 5 | 4 |
| Productivity (propanol) | 0.19 | 0.61 | 1.75 | 25.10 | 15.12 | 24.30 | 33.44 | 18.18 | 5.24 | 22.42 | 23.68 | 18.60 |

TABLE 7

| Ex/CEx//Measure | 31 | 31 | 31 | 31 | 31 | 32 | 32 | 32 | 32 | 32 |
|---|---|---|---|---|---|---|---|---|---|---|
| Time (minutes) | 60 | 120 | 180 | 240 | 300 | 60 | 120 | 180 | 240 | 300 |
| Solvent volume | 135 | 131 | 128 | 125 | 122 | 136 | 133 | 130 | 127 | 124 |
| Percent Conversion | | | | | | | | | | |
| Carbon monoxide | −12 | 4 | 17 | 26 | 35 | −1 | −1 | 3 | 13 | 19 |
| Ethylene | 64 | 73 | 78 | 82 | 84 | 64 | 68 | 69 | 72 | 73 |
| Percent Selectivity | | | | | | | | | | |
| Propanol | 50 | 54 | 57 | 56 | 57 | 26 | 32 | 36 | 35 | 35 |
| Propanal | 4 | 3 | 2 | 2 | 2 | 1 | 1 | 1 | 1 | 1 |
| Ethane | 29 | 25 | 23 | 23 | 21 | 24 | 24 | 23 | 22 | 21 |
| Carbon dioxide | 3 | 2 | 2 | 2 | 2 | 15 | 13 | 12 | 11 | 11 |
| Methanol | 1 | 1 | 1 | 1 | 1 | 1 | 1 | 1 | 1 | 1 |
| Ethanol | 0 | 1 | 1 | 1 | 2 | 1 | 1 | 2 | 2 | 2 |
| Propyl propionate | 4 | 5 | 6 | 7 | 7 | 5 | 5 | 6 | 6 | 6 |
| Propane &Propylene | 3 | 1 | 1 | 1 | 1 | 4 | 3 | 0 | 3 | 2 |
| Hydroformylated solvent products | 6 | 7 | 6 | 6 | 6 | 8 | 9 | 10 | 10 | 10 |
| Productivity, g/g cat. (propanol + propanal) | 0.07 | 0.07 | 0.065 | 0.056 | 0.052 | 0.036 | 0.031 | 0.027 | 0.023 | 0.021 |

The data presented in Table 7 show the effect of varying differing slurried catalysts on the reductive hydroformylation of ethylene in a semi-batch reactor. The data also show that ethylene conversion and selectivity to reaction products can be tuned by varying the group VIII metals, cobalt (Ex 31) and mixed cobalt/nickel (Ex 32), used to prepare the catalyst.

EX 33

Preparation of Potassium Modified Cobalt Molybdenum Catalyst Pellets

Prepare cobalt molybdenum sulfide powder generally in accordance with the procedure described in Ex 2 above. Instead of the procedure used in Ex 2, dry compound the cobalt molybdenum sulfide powder (66 wt %) with potassium carbonate powder (10 wt %), bentonite clay (20 wt %) and STEROTEX™ hydrogenated seed oil lubricant (4 wt %), each wt % being based upon total dry compound weight, and form the dry compound into cylindrical tablets measuring ⅛ inch (0.3 centimeter (cm)) (0.48 cm) to 3/16 inch in diameter and ⅛ inch (0.3 cm) to 3/16 inch (0.48 cm) in length. The tabletted dry compound has a S:Mo ratio of approximately 4:1.

Evaluate catalyst performance using a ⅜ inch (0.95 cm) outer diameter (0.277 inch (0.7 cm) inner diameter, 10.5 feet (3.2 meter (m)) 316 stainless steel tubular reactor. Pack one end of the tube with stainless steel mesh, then load the tube with sufficient ceramic spheres to fill one linear foot (0.3 m) of the tube. Follow ceramic sphere loading with 100 g of the cylindrical tablets which occupies 100 linear inches (254 cm) of the tube. Add sufficient ceramic spheres to nearly fill remaining space in the tube, then pack remaining space with stainless steel mesh. Bend the loaded tubular reactor into a coil configuration and mount it within a fluidized sand bath heater shell such that the catalyst-containing portion of the coil is centered within the fluidized sand bath heater's 60 inch (152.4 cm) middle segment.

Flow gases, either pretreatment gases or reactant gases, (delivered from gas cylinders to individual gas thermal mass controllers to provide a required gas mixture composition as determined by GC analysis) downward through the reactor tube. Use on line process GC as in Ex 1, to monitor reactant gas mixture composition and product stream composition.

Use a booster pump to increase gas pressure to 500 psig (3.45 MPa) for a pretreatment gas mixture of 80 mol % $N_2$, 20 mol % $H_2$ and 50 ppm (based on combined weight of $N_2$ and $H_2$) of hydrogen sulfide and flow the pretreatment gas mixture through the tubular reactor for 16 hours at a temperature of 280° C. to pre-treat the catalyst. Use a high pressure gas thermal mass flow controller to deliver mixed gases to the tubular reactor.

Adjust gas mixture to 10 mol % $N_2$, 45 mol % CO, 45 mol % $H_2$ and 50 ppm, based on combined weight of $N_2$, CO and $H_2$, hydrogen sulfide. Increase the temperature to 300° C. Use a booster pump to increase mixed reactant gas pressure to 1500 psig (10.3 MPa). Start a flow of ethylene in an amount as shown in Table 8 and, for all but one run, a flow of $CO_2$ in an amount as shown in Table 8, adjusting gas mixture composition with balance methane to maintain a 1:1 molar ratio of $CO:H_2$. The gases flow through the tubular reactor at a gas hourly space velocity (GHSV) of from 5500 reciprocal hours ($hr^{-1}$) to 5700 $hr^{-1}$. Table 8 also includes information about ethylene conversion percent and selectivities to materials identified in Table 8.

TABLE 8

| Ethylene in Feed (mol %) | 5.0 | 5.0 | 5.0 | 5.0 | 10.0 | 10.0 | 10.0 |
|---|---|---|---|---|---|---|---|
| $CO_2$ in Feed (mol %) | 0.0 | 1.0 | 2.5 | 5.0 | 1.2 | 2.5 | 5.0 |
| $H_2$ in Feed (mol %) | 10 | 10 | 10 | 10 | 20 | 20 | 20 |
| CO in Feed (mol %) | 10 | 10 | 10 | 10 | 20 | 20 | 20 |
| Ethylene Conversion (%) | 38.2 | 35.0 | 34.1 | 32.7 | 26.4 | 27.8 | 30.2 |
| C % Selectivities to: | | | | | | | |
| Propanol | 65.0 | 62.0 | 63.7 | 62.7 | 72.4 | 70.4 | 68.7 |
| Ethane | 9.1 | 14.1 | 13.5 | 15.5 | 7.5 | 8.1 | 9.0 |
| Propanal | 8.3 | 9.2 | 14.2 | 16.7 | 11.2 | 12.2 | 13.8 |
| $CO_2$ | 4.8 | 4.4 | 1.2 | 0.0 | 2.3 | 1.4 | 0.7 |
| Methanol | 1.3 | 0.4 | 0.8 | 0.6 | 2.2 | 2.0 | 1.7 |
| Ethanol | 0.3 | 0.3 | 0.0 | 0.0 | 1.0 | 0.8 | 0.7 |
| Butanol | 2.8 | 2.4 | 1.4 | 0.9 | 1.1 | 1.0 | 0.9 |
| Propylene | 1.7 | 1.7 | 0.9 | 1.5 | 0.9 | 0.8 | 0.8 |
| Propane | 1.8 | 1.5 | 0.9 | 0.7 | 0.3 | 0.3 | 0.3 |

The data in Table 8 illustrates that one may use an amount of $CO_2$ and still achieve beneficial conversion of ethylene using a potassium modified cobalt/molybdenum sulfide catalyst under conditions shown in this Ex 33.

EX 34

Replicate Ex 33, but eliminate CO and make changes as shown in Table 9 below. Table 9 information about ethylene conversion percent and selectivities to materials identified in Table 9.

TABLE 9

| Use of carbon dioxide with no carbon monoxide present | | | | | | |
|---|---|---|---|---|---|---|
| Ethylene in Feed (mol %) | 10 | 10 | 10 | 10 | 10 | 10 |
| $CO_2$ in Feed (mol %) | 20 | 20 | 20 | 20 | 20 | 20 |
| $H_2$ in Feed (mol %) | 20 | 20 | 20 | 32 | 38 | 38 |
| $H_2:CO_2$ Ratio | 1.0 | 1.0 | 1.0 | 1.6 | 1.9 | 1.9 |
| Temperature (° C.) | 280 | 300 | 320 | 300 | 300 | 300 |
| GHSV ($h^{-1}$) | 5700 | 5700 | 5700 | 5700 | 5700 | 4100 |
| Ethylene Conversion (%) | 16.9 | 25.7 | 36.4 | 29.6 | 31.5 | 43.6 |
| $CO_2$ Conversion (%) | 12.8 | 14.8 | 16.3 | 18.9 | 20.6 | 21.2 |
| C % Selectivities to: | | | | | | |
| Propanol | 40.5 | 38.6 | 33.3 | 43.8 | 45.3 | 44.3 |
| Ethane | 53.5 | 56.7 | 62.2 | 51.7 | 50.2 | 51.7 |
| Propanal | 5.6 | 3.8 | 3.3 | 3.3 | 2.9 | 2.3 |
| Methanol | 0.1 | 0.4 | 0.3 | 1.0 | 1.3 | 1.2 |
| Ethanol | 0.0 | 0.0 | 0.0 | 0.0 | 0.0 | 0.0 |
| Butanol | 0.0 | 0.0 | 0.1 | 0.1 | 0.1 | 0.1 |
| Propylene | 0.0 | 0.2 | 0.5 | 0.1 | 0.1 | 0.2 |
| Propane | 0.0 | 0.0 | 0.2 | 0.0 | 0.0 | 0.1 |

The data in Table 9 demonstrate that $CO_2$ may be used as a complete replacement for CO in the conversion of ethylene to propanol.

As shown in the Examples, one can use a S:Mo ratio of approximately 2:1 or 4:1 with acceptable results. One may use a ratio other than 2:1 or 4:1 and also obtain acceptable results.

What is claimed is:

1. A method for converting an alkylene to a product stream that comprises an alkanol, the method comprising subjecting a gaseous combination of a) an alkylene selected from ethylene, propylene or a combination thereof, b) carbon monoxide, c) hydrogen and, optionally, d) at least one hydrocarbon or gas diluent other than ethylene or propylene to reductive hydroformylation conditions in combination with a solid phase, sulfided, heterogeneous catalyst, such combination being sufficient to convert ethylene to propanol and propylene to butanol, said catalyst comprising at least one Group VIII metal, at least one Group VI metal, at least one alkali metal and sulfur.

2. The method of claim 1, wherein the reductive hydroformylation conditions comprise a reaction temperature of from 200 degrees centigrade to 400 degrees centigrade and a reaction pressure of from 100 pounds per square inch gauge (689.5 kilopascals) to 3000 pounds per square inch gauge (20.7 megapascals).

3. The method of claim 1, wherein the reductive hydroformylation conditions further comprise a gaseous combination gas hourly space velocity of from 1000 $hr^{-1}$ to 15,000 $hr^{-1}$.

4. The method of claim 1, wherein the Group VIII metal is at least one of a group consisting of iron, cobalt and nickel.

5. The method of claim 1, wherein the alkali metal is at least one of a group consisting of lithium, sodium, potassium, cesium and rubidium.

6. The method of claim 1, wherein the Group VI metal is molybdenum.

7. The method of claim 6, wherein the Group VIII metal is at least one of cobalt and nickel.

8. The method of claim 1, wherein the catalyst comprises cobalt as the Group VIII metal, molybdenum as the Group VI metal, at least one of potassium and cesium as the alkali metal and sulfur.

9. The method of claim 1, wherein the catalyst is supported on a catalyst support, the catalyst support being selected from a group consisting of silica, titania, zirconia, zinc oxide, magnesium oxide, lanthanum oxide, manganese oxide, activated carbon, and hydrotalcite (clays).

10. The method of claim 1, wherein the gaseous combination further comprises at least one of carbon dioxide and methanol.

11. The method of claim 1, wherein the gaseous combination further comprises a sulfiding agent selected from a group consisting of hydrogen sulfide, an alkyl mercaptan, a dialkyl sulfide or a dialkyl disulfide.

12. The method of claim 1, wherein the combination also yields an amount of an aldehyde selected from propionaldehyde and butyraldehyde and, optionally, at least a portion of the propionaldehyde is converted to propanol, or at least a portion of the butyraldehyde is converted to butanol, or at least a portion of propionaldehyde is converted to propanol and at least a portion of the butyraldehyde is converted to butanol by one or more of additional time of exposure to the catalyst or exposure to a second stage hydrogenation catalyst.

13. The method of claim 1, wherein the catalyst is present as a slurry of catalyst particles in a non-reactive fluid selected from a group consisting of paraffin solvents, non-paraffin alkane solvents, and oxygenate solvents including products of the process, non-paraffin alkane solvents, and oxygenate solvents.

* * * * *